(12) United States Patent
Hatten

(10) Patent No.: US 10,328,112 B2
(45) Date of Patent: Jun. 25, 2019

(54) ABRASIVE PEDICULICIDE COMPOSITIONS COMPRISING MATERIALS, KITS, AND METHODS OF USE

(71) Applicant: Michael S. Hatten, Des Moines, IA (US)

(72) Inventor: Michael S. Hatten, Des Moines, IA (US)

( * ) Notice: Subject to any disclaimer, the term of this patent is extended or adjusted under 35 U.S.C. 154(b) by 0 days.

(21) Appl. No.: 16/100,389

(22) Filed: Aug. 10, 2018

(65) Prior Publication Data

US 2019/0160127 A1    May 30, 2019

Related U.S. Application Data

(60) Provisional application No. 62/592,007, filed on Nov. 29, 2017.

(51) Int. Cl.
| | |
|---|---|
| *A61K 36/00* | (2006.01) |
| *A61K 36/52* | (2006.01) |
| *A61K 9/00* | (2006.01) |
| *A61Q 5/02* | (2006.01) |
| *A61P 33/14* | (2006.01) |

(52) U.S. Cl.
CPC ............ *A61K 36/52* (2013.01); *A61K 9/0014* (2013.01); *A61P 33/14* (2018.01); *A61Q 5/02* (2013.01)

(58) Field of Classification Search
CPC ....................................................... A61K 36/00
USPC ........................................................... 424/725
See application file for complete search history.

(56) References Cited

U.S. PATENT DOCUMENTS

| | | |
|---|---|---|
| 2002/0025336 A1 | 2/2002 | McGuire et al. |
| 2004/0092606 A1 | 5/2004 | McPartland |
| 2005/0004233 A1 | 1/2005 | Bessette et al. |
| 2007/0295350 A1 | 12/2007 | Shelton |
| 2010/0286097 A1 | 11/2010 | Mercieca et al. |
| 2011/0070323 A1 | 3/2011 | Pesso |
| 2012/0071444 A1 | 3/2012 | Cooper |
| 2012/0093949 A1 | 4/2012 | Steinberg |
| 2013/0072455 A1 | 3/2013 | Campbell et al. |
| 2014/0296182 A1 | 10/2014 | Levin et al. |
| 2015/0164066 A1 | 6/2015 | Harding et al. |
| 2016/0029625 A1 | 2/2016 | Kennedy et al. |
| 2017/0049110 A1 | 2/2017 | Kolender et al. |
| 2017/0094963 A1 | 4/2017 | Enan |
| 2017/0118998 A1 | 5/2017 | Bessette et al. |

*Primary Examiner* — Michael V Meller
(74) *Attorney, Agent, or Firm* — McKee, Voorhees & Sease, PLC

(57) ABSTRACT

The present technology relates generally to pediculicide compositions, method of use, and kits thereof. In particular, disclosed herein is improved pediculicide compositions comprising one or more abrasive materials. The present technology is useful for treating human head lice, *Pediculus humanus capitis*, through abrasives to break lice and its nits. Preferably, the compositions lack toxic and regulated pediculicide active ingredients, are free of preservatives, and require only a single application to hair.

16 Claims, No Drawings

ABRASIVE PEDICULICIDE COMPOSITIONS COMPRISING MATERIALS, KITS, AND METHODS OF USE

CROSS REFERENCE TO RELATED APPLICATIONS

This application claims priority under 35 U.S.C. § 119 to U.S. provisional application Ser. No. 62/592,007, filed Nov. 29, 2017, which is herein incorporated by reference in its entirety.

FIELD OF THE INVENTION

The present technology relates generally to pediculicide compositions, method of use, and kits thereof. In particular, disclosed herein are improved pediculicide compositions comprising one or more abrasive materials, methods and kits thereof. The present technology is useful for treating human head lice, *Pediculus humanus capitis*, through abrasives, to break up and disintegrate lice and nits, in a human infestation.

BACKGROUND OF THE INVENTION

The following description is provided to assist the understanding of the reader. None of the information provided or references cited is admitted to be prior art to the present technology.

Head lice are parasitic insects that infest a person's head and neck. Lice live off the scalp by drawing small amounts of blood. Each louse can lay about 7 to 10 eggs, also known as nits, every 7 to 10 days, thereby allowing the lice to multiply relatively rapidly. Prior to the nits hatching, there is a strong glue-like bond formed between the shaft of the hair and the nits, which makes it very difficult to separate the nits from the hair and remove the nits.

Various compositions, also known as pediculicides or pediculicidal compositions, methods of using pediculicides, and kits including pediculicides have been used to treat head lice infestations. Existing methods of treatment of the lice-infested hair include using gels, pesticidal liquids, shampoos, conditioners, or other compositions, together with certain means such as combs, for mechanically removing lice and nits killed with pediculicides. Laboratory and clinical studies have found that many of the pediculicides in the market are either not fully effective or are ineffective, even when they are used according to the instructions.

Some of these methods include long wait times before the composition can be washed away or removed from the hair. Some require multiple treatments over several days or weeks, or have difficulty in combing out lice and nits after application of the pediculicide, i.e., if the pediculicide is too viscous for a comb to pass through; or if the treatment causes the hair to become tangled; or if the treatment applied is too oily and difficult to remove by conventional shampooing. Some existing treatment methods may only be partially effective, such as by killing lice but having no impact on the nits (ovicidal activity) or the ability to remove the nits from the hair. Many of the prior non-pesticidal treatments have focused on suffocation or desiccation of the lice and are unable to remove the eggs satisfactorily. Thus, adult lice are removed from the hair with some eggs, but treatments must be repeated multiple times to continue to remove the adult lice until all the eggs have hatched.

Furthermore, many pediculicides include regulated chemicals that can be toxic and harmful under certain circumstances or in higher concentrations, particularly when used on school age children. Pediculicides often comprise insecticides such as organochlorines (lindane), organophosphates (malathion), carbamates (carbaryl), pyrethrins (pyrethrum), and pyrethroids (permethrin, phenothrin, bio-allethrin).

In addition, certain strains of lice are progressively becoming resistant to the active ingredients used in some existing pediculicides, thereby necessitating more pediculicides with different chemicals, leading to additional toxicity. Thus, some pediculicides may rapidly lose their efficacy because of the development of resistance, which may be due to overuse. In fact, resistance of head lice to insecticides such as lindane, malathion, phenothrin and permethrin has been reported. A further problem with such compositions is that some chemicals used in pediculicides cause additional scalp irritation. The need for multiple products and/or steps are also caused by the fact that the products are often not applied properly and/or all lice and nits are not completely removed.

Thus, there is a need for new treatments for lice infestations (Pediculosis), that can kill and remove both the adult lice and their eggs. Additionally, since consumers are becoming increasingly conscious of the products they are using on themselves and their families, a simpler and safer composition that is still effective without a long ingredient list of toxic chemicals, resulting in a reduced treatment time, easier or simplified treatment procedure, i.e., by reducing the number of products needed or the steps performed, thus providing easy removal of both the lice and nits. In other words, there is a need for lice treatment methods, compositions, and kits that do not include many toxic or synthetic chemicals and that can remove and kill both adult lice and the eggs.

Accordingly, it is an objective of the claimed invention to develop a pediculicide without synthetic, toxic chemicals and preservatives and with capability to kill both lice and nits.

Still a further object of the invention is to provide a pediculicide that only needs to be used a single time for effective treatment and removal of head lice.

Other objects, advantages and features of the present invention will become apparent from the following specification.

BRIEF SUMMARY

The present technology provides an improved pediculicide comprising one or more abrasive materials. As a result, the present technology, can kill both lice and nits in one simple application. Unlike prior art, the improved pediculicide does not include any preservatives and unnatural chemicals, yet is very effective to remove both lice and nits.

An advantage of the invention is that the disclosed compositions can kill both lice and nits in one application. And the compositions disclosed herein are free of toxic chemicals and contains only ingredients originated from nature or natural plants. It is an advantage of the present invention that the disclosed pediculicides are free of preservatives.

A preferred embodiment is a lice-treatment composition comprising between about 60 wt. % and about 95 wt. % of a base carrier, between about 1 wt. % and about 10 wt. % of a solvent, and between about 0.5 wt. % and about 7 wt. % of an abrasive, wherein the composition is gel, liquid, lotion, or cream.

Another preferred embodiment is a pediculicide composition comprising from about 60 wt-% to about 95 wt-% of a base carrier, wherein the base carrier is a middle chain triglyceride, or combination thereof; from about 2 wt-% to about 10 wt-% of a solvent, wherein the solvent comprises d-limonene, citrus oils, olive oil, or mixture thereof; from about 0.5 wt-% to about 5 wt-% of a humectant comprising triethylene glycol, tripropylene glycol, propylene glycol, polypropylene glycol, glycerin, sorbitol, hexylene glycol, butylene glycol, collagen, or a mixture thereof; from about 1 wt-% to about 10 wt-% of an abrasive, wherein the abrasive comprises a nut shell, fruit pit, hard mineral, synthetic stone, polyethylene beads, or mixture thereof; and from about 1 wt-% to about 12 wt-% of a thickener wherein the thickener comprises diatomaceous earth, fused silica, or a mixture thereof; wherein the pediculicide composition is a liquid, gel, lotion or cream.

Still another embodiment is a head lice treatment kit comprising an applicator brush and/or lice comb and a pediculicide composition comprising from about 60 wt-% to about 95 wt-% of a base carrier, wherein the base carrier is a middle chain triglyceride fractionated coconut oil; from about 2 wt-% to about 10 wt-% of a solvent, wherein the solvent comprising d-limonene, citrus oils, olive oil, or mixture thereof; from about 0.5 wt-% to about 5 wt-% of a humectant comprising triethylene glycol, tripropylene glycol, propylene glycol, polypropylene glycol, glycerin, sorbitol, hexylene glycol, butylene glycol, collagen, or a mixture thereof; from about 1 wt-% to about 10 wt-% of an abrasive, wherein the abrasive comprises a nut shell, fruit pit, hard mineral, synthetic stone, polyethylene beads, or mixture thereof; and from about 1 wt-% to about 12 wt-% of a thickener, wherein the thickener comprises diatomaceous earth, fused silica, or a mixture thereof; wherein the pediculicide composition is a liquid, gel, lotion, or cream, and the composition has a viscosity between about 3500 cps and about 100,000 cps.

Yet another embodiment is a method of preparing a liquid, gel, lotion, or cream pediculicide composition, the method comprising (a) adding a base carrier, a solvent, and a humectant; (b) mixing; (c) adding an abrasive; (d) mixing; (e) adding a thickener; and (f) mixing to form a pediculicide composition; wherein the pediculicide composition comprises from about 60 wt-% to about 95 wt-% of a base carrier, from about 2 wt-% to about 10 wt-% of a solvent, from about 0.5 wt-% to about 5 wt-% of a humectant; from about 1 wt-% to about 10 wt-% of an abrasive, and from about 1 wt-% to about 12 wt-% of a thickener.

In yet another aspect, the present technology is a method of killing lice and nits, the method comprises contacting lice infested hair with any of the disclosed pediculicides herein.

In another aspect, the present technology is a kit, the kit comprises any one of the disclosed pediculicides herein, applicator brush and or lice comb.

The forgoing summary is illustrative only and is not intended to be in any way limiting. In addition to the illustrative aspects, embodiments and features described above, further aspects, embodiments, and features of the present technology will become apparent to those skilled in the art from the following drawings and the detailed description, which shows and describes illustrative embodiments of the present technology.

DETAILED DESCRIPTION OF THE PREFERRED EMBODIMENT

The illustrative embodiments described in the detailed description and claims are not meant to be limiting. Other embodiments may be utilized, and other changes may be made, without departing from the spirit or scope of the subject matter presented here. Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

DEFINITIONS

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The use of the terms "a" and "an" and "the" and similar referents in the context of describing the elements (especially in the context of the following claims) are to be construed to cover both the singular and the plural, unless otherwise indicated herein or clearly contradicted by context.

The term "about," as used herein, refers to variation in the numerical quantity that can occur, for example, through typical measuring techniques and equipment, with respect to any quantifiable variable, including, but not limited to, mass, volume, and time. Further, given solid and liquid handling procedures used in the real world, there is certain inadvertent error and variation that is likely through differences in the manufacture, source, or purity of the ingredients used to make the compositions or carry out the methods and the like. The term "about" also encompasses these variations. Whether or not modified by the term "about," the claims include equivalents to the quantities.

All units, prefixes, and symbols may be denoted in its SI accepted form.

Ratio, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited.

Numeric ranges recited within the specification are inclusive of the numbers defining the range and include each integer within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4¾ This applies regardless of the breadth of the range.

The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "consisting essentially of" means that the compositions, kits, and methods may include additional components, ingredients, and steps, but only if the additional components, ingredients, and steps do not materially alter the basic and novel characteristics of the claimed compositions, kits, and methods.

As used herein, the term "free of an ingredient" refers to a composition or mixture that does not contain the ingredient or to that the ingredient has not been added. Should the ingredient be present through contamination, the amount of the ingredient shall be less than 0.5 wt-%. More preferably, the amount of the ingredient is less than 0.1 wt-%.

As used herein, the term "plant" includes, but is not limited to, seeds, pits, nuts, plants or crops grown or stored in a greenhouse, house plants, and the like. Plant products include many animal feeds.

The term "weight percent," "wt. %," "wt-%," "percent by weight," "% by weight," and variations thereof, as used herein, refer to the concentration of a substance as the weight of that substance divided by the total weight of the composition and multiplied by 100.

Pediculicide Composition

The compositions described herein are types of pediculicides. Pediculicides, as used herein, refer broadly to compositions that are applied to hair or scalp to treat human lice infestations (*Pediculus humanus capitis*). The pediculicide compositions can be in a form of shampoo, conditioner, or other hair product. Preferably, the pediculicide compositions are conditioners. Preferably, the compositions described herein are prepared as a gel, liquid, lotion, or cream.

The pediculicide compositions described herein address the problems existing in the art of nit hair shaft adhesive by dissolving the attachments between the nits and the patient's hair follicle while the abrasive acts to splinter and rip apart and kill the adult lice and the nits. Beneficially, the compositions can be prepared with ingredients such that they are natural, do not include toxic ingredients, and are free of typical toxicants and preservatives. The pediculicide compositions can comprise a base carrier, a solvent, and an abrasive. The compositions can optionally comprise a variety of additional ingredients added to provide desired properties, such additional ingredients can include, but are not limited to, a humectant, an emulsifier, thickener, moisturizer, an antioxidant, a dye, a fragrance or a mixture thereof. Table 1 provides exemplary concentrations for the pediculicide compositions.

Various ingredients suitable for the pediculicide compositions are discussed further herein.

TABLE 1

| Ingredients | Concentration in weight percentage | | |
|---|---|---|---|
| | Preferred | More Preferred | Most Preferred |
| Base Carrier | 60-95 | 70-90 | 80-90 |
| Solvent(s) | 1-10 | 2-9 | 3-7 |
| Abrasive | 0.5-7 | 0.5-5 | 0.7-2 |
| Thickener(s) | 0.5-12 | 1-10 | 3-7 |
| Other ingredients | 0-20 | 0.05-15 | 0.1-10 |
| Viscosity (cps) | 3500-100,000 | 4000-75,000 | 5000-65,000 |

Abrasive

The improved pediculicides disclosed herein comprise an abrasive or abrasive material. The abrasive rips and ruptures the nit shells and lice exoskeleton after the abrasive is contacted with nits or lice, effectively disintegrating adults and eggs. The addition of an abrasive in a pediculicide improves the pediculicide's effectiveness and makes multiple applications of a pediculicide unnecessary, because the abrasive can effectively, and preferably completely, eliminate nits together with lice with one application.

Abrasive or abrasive material as used herein refers to a material that is used to cut, grind, polish, piece, or rip other softer material. In general, an abrasive is a material that is used to degrade, modify, shape or finish a workpiece through rubbing which leads to part of the workpiece being worn away by friction. Used in a pediculicide composition, this abrasive friction is used to rip, break, fracture, crumble or disintegrate nits and lice's exoskeleton in order to kill them.

Preferred abrasives, include, but are not limited to, a hard, natural mineral, synthetic stone, polyethylene beads, or other materials. Synthetic abrasive materials can be chemically and physically identical to naturally occurring minerals although they have been synthesized. Certain softer minerals can also be included, such as calcium carbonate. Natural materials suitable as abrasives, include but are not limited to, nut shells, fruit pits, etc. These abrasives are discussed further herein.

Abrasive is usually crushed or already of a sufficiently small size (anywhere from macroscopic grains as large as about 2 mm to microscopic grains about 0.001 mm in diameter) to permit their use as an abrasive. The crushed abrasive grains, commonly called grit, have rough edges, often terminating in points which will decrease the surface area in contact and increase the localized contact pressure. The abrasive and the material to be worked are brought into contact while in relative motion to each other. Force applied through the grains causes fragments of the worked material to break away, while simultaneously smoothing the abrasive grain and/or causing the grain to work loose from the rest of the abrasive.

The effectiveness of an abrasive to cut into a soft material or into nits or lice is affected by its hardness, grain size, adhesion between grains, contact force, loading, and other material in the same composition. A much harder abrasive will cut faster and deeper. Larger grains will cut faster as they also cut deeper. Adhesion determines how quickly grains are lost from the abrasive and how soon fresh grains, if present, are exposed. Of course, more and longer contact force causes faster abrasion or penetration. An applicator brush used to properly distribute product on the affected area can increase abrasive efficacy. More abrasive in a composition generally increases effectiveness because a less chance for the softer material to fill the gap between worn abrasive. Use of other material can affect the effectiveness as well.

Some naturally occurring abrasives include, but are not limited to calcite (calcium carbonate), emery (impure corundum), diamond dust (synthetic diamonds are used extensively), novaculite, pumice, rouge, sand, corundum, garnet, sandstone, Tripoli, powdered feldspar, staurolite, walnut shells, apricot pits, peach pits and mixtures thereof.

In the disclosed pediculicides, preferred abrasives are those originated from plant or inert naturally occurring abrasives.

In some embodiments, the composition comprises from about 1 wt-% to about 10 wt-% of the abrasive. In some other embodiments, the composition comprises from about 2 wt-% to about 10 wt-%, from about 4 wt-% to about 10 wt-%, from about 5 wt-% to about 10 wt-%, from about 6 wt-% to about 10 wt-%, from about 7 wt-% to about 10 wt-%, from about 8 wt-% to about 10 wt-%, from about 9 wt-% to about 10 wt-%, from about 1 wt-% to about 3 wt-%, from about 1 wt-% to about 5 wt-%, from about 1 wt-% to about 7 wt-%, from about 1 wt-% to about 9 wt-%, from about 4 wt-% to about 8 wt-%, from about 6 wt-% to about 8 wt-%, from about 4 wt-% to about 6 wt-%, about 1 wt-%, about 2 wt-%, about 4 wt-%, about 6 wt-% to about 8 wt-%, about 10 wt-%, or any value there between of the abrasive.

Antioxidant

The compositions can optionally comprise an antioxidant. Preferred antioxidants comprise mixed tocopherols. If included, the antioxidants are preferably in an amount between about 0.05 wt-% and about 1 wt-%.

Base Carrier Base carriers that can be used in the disclosed pediculicides includes, but not limited to fatty acids, Medium Chain (C6-C12) Triglycerides (MCT), MCT from coconut oil or coconut fractionated Medium Chain Triglycerides (MCT), or combination thereof. In coconut fractionated MCT, the lauric (C12) acid is removed, leaving only the capric (decanoic or C10) acid and caprylic (C8) acids. Usually, MCT oil contains about three-quarters caprylic acid and one-quarter capric acid. Preferably, the base carrier can also provide moisturizing and/or emollient properties to the composition. A preferred base carrier is a medium chain triglyceride fractionated coconut oil.

In some embodiments, the composition comprises from about 60 wt-% to about 95 wt-% of the base carrier. In some other embodiments, the composition comprises from about 65 wt-% to about 95 wt-%, from about 70 wt-% to about 95 wt-%, from about 75 wt-% to about 95 wt-%, from about 80 wt-% to about 95 wt-%, from about 85 wt-% to about 95 wt-%, from about 90 wt-% to about 95 wt-%, from about 60 wt-% to about 70 wt-%, from about 60 wt-% to about 80 wt-%, from about 60 wt-% to about 90 wt-%, about 60 wt-%, about 65 wt-%, about 70 wt-%, about 75 wt-%, about 80 wt-%, about 85 wt-%, about 90 wt-%, about 95 wt-%, or any value there between.

Dye/Colorant

The compositions can optionally comprise a dye or colorant. If included, the dye or colorant is preferably in an amount between about 0.05 wt-% and about 1 wt-%.

Emulsifier

Emulsifiers can also be included in the pediculicide compositions. A preferred emulsifier is hydrogenated castor oil, terpene, or another naturally occurring emulsifier. If an emulsifier is included in the compositions, the base carrier can be reduced. A preferred range for the emulsifier is between about 0.5 wt. % and about 10 wt. %.

Fragrance

The compositions can optionally comprise a fragrance. Preferred fragrances comprise amyl cinnamal, benzyl salicylate, citronellol, gardenia, hexyl cinnamal, lavender, lemongrass limonene, linalool, menthol, and mixtures thereof. A most preferred fragrance is lemongrass verbena. If included, the fragrance is preferably in an amount between about 0.05 wt-% and about 1 wt-%.

Humectant

Humectants that can be used in the disclosed pediculicides include, but not limited to triethylene glycol, tripropylene glycol, propylene glycol, polypropylene glycol, glycerin, sorbitol (sugar alcohol), hexylene glycol, butylene glycol, collagen, or a mixture thereof. Glycerin is one of the most popular humectants used because it produces the desired result fairly frequently and is low in cost.

In some embodiments, the composition comprises from about 0.5 wt-% to about 5 wt-% of the humectant. In some other embodiments, the composition comprises about 0.5 wt-%, about 1 wt-%, about 2 wt-%, about 3 wt-%, about 4 wt-%, about 5 wt-%, or any value there between of the humectant.

Moisturizer

A moisturizer can optionally be included in the compositions. Preferred moisturizers include essential oils and/or essential oil complexes. Preferred essential oils include, but are not limited Argan, Sesame, Jojoba, Grapeseed, Sweet Almond, Tea Tree Oil, and mixtures thereof. If included in the compositions, the moisturizer is preferably in an amount between about 0.01 wt-% and about 5 wt-%.

Solubilizer

A solubilizer can optionally be included in the compositions. Preferred solubilizers include, but are not limited to, an organic acid, a polysorbate, a propanediol, a safflower oleosome, or a mixture thereof. Preferred organic acids, include but are not limited to, resin acids such as abietic acid, neoabietic acid, dyhydroabietic acid, palustric acid, levopimaric acid, and/or derivatives and salts thereof. A preferred solubilizer is an abietate such as hydgrogenated methyl abietate or hydrogenated glyceryl abietate.

In an embodiment comprising a solubilizer, the solubilizer is preferably in an amount between about 0.5 wt. % to about 10 wt. %, more preferably from about 1 wt. % to about 10 wt. %, most preferably between about 2 wt. % and about 4 wt. %.

Solvent

Solvents that can be used in the disclosed pediculicides include, but not limited to, d-limonene, citrus oils, olive oil, other naturally derived solvents, or combination thereof.

Preferably the solvent comprises from about 2 wt-% to about 10 wt-% of the composition. More preferably, the composition comprises from about 3 wt-% to about 10 wt-%, from about 4 wt-% to about 10 wt-%, from about 5 wt-% to about 10 wt-%, from about 6 wt-% to about 10 wt-%, from about 7 wt-% to about 10 wt-%, from about 8 wt-% to about 10 wt-%, from about 9 wt-% to about 10 wt-%, from about 2 wt-% to about 3 wt-%, from about 2 wt-% to about 5 wt-%, from about 2 wt-% to about 7 wt-%, from about 2 wt-% to about 9 wt-%, from about 4 wt-% to about 8 wt-%, from about 6 wt-% to about 8 wt-%, from about 4 wt-% to about 6 wt-%, about 2 wt-%, about 4 wt-%, about 6 wt-% to about 8 wt-%, about 10 wt-%, or any value there between of the solvent.

Thickener

Thickeners used in the disclosed pediculicides include, but not limited to, diatomaceous earth product, fumed silica, or combination thereof. Diatomaceous earth usually has a particle size ranging from less than 3 micrometers to more than 1 millimeters, but typically 10 to 200 micrometers. Depending on the granularity, this powder can have an abrasive feel, similar to pumice powder, and has a low density as a result of its high porosity. The typical chemical composition of oven-dried diatomaceous earth is 80 to 90% silica, with 2 to 4% alumina (attributed mostly to clay minerals) and 0.5 to 2% iron oxide. Fumed silica (CAS number 112945-52-5), also known as pyrogenic silica because it is produced in a flame, consists of microscopic droplets of amorphous silica fused into branched, chainlike, three-dimensional secondary particles which then agglomerate into tertiary particles.

In some embodiments, the composition comprises from about 1 wt-% to about 12 wt-% of the thickener. In some other embodiments, the composition comprises about 2 wt-% to about 12 wt-%, from about 4 wt-% to about 12 wt-%, from about 5 wt-% to about 12 wt-%, from about 6 wt-% to about 12 wt-%, from about 7 wt-% to about 12 wt-%, from about 8 wt-% to about 12 wt-%, from about 9 wt-% to about 12 wt-%, from about 10 wt-% to about 12 wt-%, from about 1 wt-% to about 3 wt-%, from about 1 wt-% to about 5 wt-%, from about 1 wt-% to about 7 wt-%, from about 1 wt-% to about 9 wt-%, from about 1 wt-% to about 11 wt-%, from about 4 wt-% to about 8 wt-%, from about 6 wt-% to about 8 wt-%, from about 4 wt-% to about 6 wt-%, about 1 wt-%, about 2 wt-%, about 4 wt-%, about 6 wt-% to about 8 wt-%, about 10 wt-%, about 11 wt-%, about 12 wt-%, or any value there between of the thickener.
Water In some embodiments, the compositions can comprise water. If water is included in a composition, it is preferably in an amount between about 0.1 wt. % and about 35 wt. %, more preferably between about 1 wt. % and about 30 wt. %, and most preferably between about 2 wt. % and about 25 wt. %. In some embodiments, the compositions have minimal water. For example, in a preferred embodiment, the compositions have less than about 15 wt. % water, less than about 14 wt. % water, less than about 13 wt. % water, less than about 12 wt. % water, less than about 11 wt. % water, less than about 10 wt. % water, less than about 9 wt. % water, less than about 8 wt. % water, less than about 7 wt. % water, less than about 6 wt. % water, less than about 5 wt. % water, less than about 4 wt. % water, less than about 3 wt. % water, or less than about 2 wt. % water. In a preferred embodiment, the compositions are substantially free of water and contain less than about 1 wt. % water, less than about 0.5 wt. % water, less than about 0.1 wt. % water.

Exemplary Pediculicide Compositions

In one aspect, the present technology is a pediculicide composition that comprises an abrasive, wherein the composition is a pediculicide.

In some embodiments, the composition further comprises a thickener. In some other embodiments, the composition further comprises a solvent. In yet some embodiments, the composition further comprises an emollient or moisturizer. In yet some other embodiments, the composition further comprises a humectant.

In some embodiments, in addition to the abrasive, the composition further comprises one or more insecticide, a toxic pediculicide, a toxic pesticide, and/or a toxicant. In some other embodiments, the composition further comprises one or more silicon based materials.

Generally speaking, adding an abrasive into an existing pediculicide would enhance the effectiveness of the existing pediculicide, because the abrasive would not only complement the capability of the existing pediculicide to kill or remove lice, but also kill or remove nits.

In some embodiments, the abrasive is grinded walnut shell. In some other embodiments, the abrasive is a synthetic abrasive. In some other embodiments, the thickener is diatomaceous earth, fused silica, or a combination thereof.

In some other embodiments, the base carrier is a middle chain triglyceride, fractionated coconut oil (MCT) or combination thereof. In yet some other embodiments, the base carrier is coconut fractionated middle chain triglyceride (MCT).

In some embodiments, the humectant is preferably glycerin. In some other embodiments, the solvent is preferably d-limonene.

The compositions are preferably free of toxic pediculicides, toxic pesticides, and/or toxicants. In some embodiments, the composition is free of preservatives. In some other embodiments, the composition is free of water. In yet some other embodiments, the composition is free of both preservatives and water. In a preferred embodiment, the compositions are anhydrous.

In some embodiments, the composition further comprises from about 0.05 wt-% to about 2 wt-% of a fragrance, antioxidant, or both.

In another aspect, the present technology is a pediculicide composition that comprises from about 60 wt-% to about 95 wt-% of a base carrier; from about 2 wt-% to about 10 wt-% of a solvent; from about 0.5 wt-% to about 5 wt-% of a humectant; from about 1 wt-% to about 10 wt-% of an abrasive; and from about 1 wt-% to about 12 wt-% of a thickener.

In some embodiments, the base carrier is a middle chain triglyceride, naturally derived oil or combination thereof. In some other embodiments, the solvent is d-limonene. In yet some other embodiments, the abrasive is walnut shell. In other embodiments, the humectant is glycerin. In some embodiments, the thickener is fumed silica, diatomaceous earth, or combination thereof. In some embodiments, the composition is free of preservatives, free of water, or both.

In some embodiments, the composition has a viscosity of from about 3500 to about 100,000 cps. Preferably from about 4000 cps to about 75,000 cps. More preferably from about 5000 cps to about 65,000 cps. Most preferably from about 6500 to about 60,000 cps.

Methods of Preparing the Pediculicide Compositions

To prepare the compositions, the various ingredients can be combined and mixed. Preferably, the ingredients are added stepwise and mixed. Mixing can be performed continuously and/or after the addition of each ingredient. In a preferred embodiment, all of the liquid ingredients are added and mixed; this would typically exclude the abrasive and some types of thickeners. Preferably mixing is performed until the ingredients are thoroughly mixed until the mixture appears uniform. The amount of time needed to mix the ingredients can vary depending on the type of mixer, amount of ingredients, and mixing intensity. Typically mixing will be performed for a time between about 5 minutes and about 60 minutes, more preferably between about 10 minutes and about 30 minutes. Mixing phases for the formulation may include a heating phase. After sufficiently mixing the liquid ingredients, the abrasive and/or thickener can be added and mixed. The mixing should continue until the abrasive and/or thickener are hydrated. Typically, this can take from about 5 minutes to about 60 minutes, preferably between about 15 minutes and about 45 minutes. In a preferred embodiment, the abrasive is added prior to the thickener, mixed, and allowed to hydrate. Following completed hydration of the abrasive, the thickener is added, mixed, and allowed to hydrate. The final product should be uniformly mixed with no lumps and no dry ingredients remaining.

The compositions can be prepared in a continuous process or batch process. The compositions can be bottled or otherwise packaged.

In a preferred embodiment, the compositions are added to a kit comprising an applicator brush and/or lice comb. Optionally, the kit can include goggles or another eye protectant.

Methods of Using the Compositions

In yet another aspect, the present technology is a method of killing lice and nits, the method comprises contacting hair with any of the disclosed pediculicides herein. In some embodiments, the method further comprises using an applicator brush to distribute product and combing the hair with a lice comb. In some other embodiments, the method further comprises shampooing and rinsing the hair.

Preferably, the composition is contacted with the hair by adding the composition to the patient's wet hair, uniformly distributing product throughout the hair, with the applicator brush, and allowing the composition to set in the hair for sufficient time to dissolve the connections between the nits and hair follicles. A preferred amount of time for the composition to contact the patient's hair is at least about 5 minutes, more at least about 10 minutes, at least about 15 minutes, at least about 25 minutes, at least about 30 minutes, at least about 45 minutes. Typically, the compositions need not be applied for more than 90 minutes, more than 75 minutes, more than 60 minutes.

After the application waiting period, the patient's hair should be vigorously brushed in several directions, with the applicator brush for at least 2 minutes, 3 minutes, 4 minutes, 5 minutes, at least 10 minutes, or at least 15 minutes. Patient may add water if needed to assist in brushing. This can assist with shredding the adult lice and nits as well as with removal of the abrasive from the patient's hair.

After brushing the patient can optionally allow the composition to remain in their hair for an additional period of time, preferably at least 2 minutes, at least 3 minutes, at least 4 minutes, at least 5 minutes, at least 10 minutes, or at least 15 minutes. The patient can optionally repeat brushing and/or resting again.

After brushing or resting, the patient can then rinse the composition from their hair. Preferably, the rinsing step is accompanied by brushing or combing.

After rinsing the composition from the hair, preferably the patient shampoos the hair with a regular shampoo. Preferably, the shampooing and rinsing of shampoo is again accompanied by brushing with the applicator brush. After rinsing, patient should inspect for any remaining lice or nits and use fine tooth lice comb to remove. The hair can optionally be washed with shampoo and rinsed again. Once shampooing and rinsing is complete, the hair is preferably combed. The hair can optionally be dried.

EXAMPLES

Embodiments of the present invention are further defined in the following non-limiting Example. It should be understood that this Example, while exemplifying a preferred embodiment of the invention, is given by way of illustration only. From the above discussion and this Example, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

Preparation of an Exemplary Pediculicide Compositions

Exemplary pediculicide compositions exemplifying preferred embodiments of the invention were made with the ingredients listed in Tables 2A and 2B below.

The composition in Table 2A was prepared as follows. The ingredients were added to a stainless-steel mix vessel stepwise from coconut fractionated MTC to glycerin to form a mixture. The mixture was mixed until the liquid components appeared uniformly mixed (for about fifteen to twenty minutes). With agitation, walnut shells and diatomaceous earth were added to the mixture. Mixing was continued until the ingredients appeared homogenous (about 30 minutes) and the walnut shells appeared hydrated. The fumed silica was then added and mixed with other ingredients until the composition was lump free and the fumed silica appeared hydrated.

TABLE 2A

Ingredients and concentration in an exemplary pediculicide.

| Chemical Component | Function | Concentration (wt. %) |
|---|---|---|
| Fractionated Coconut Oil MTC-60/401 (New Directions Coconut Products) | Base Carrier | 70-90 |
| d-Limonene (Citrus-Solv ™ Prime, Florida Chemical) | Solvent | 3-7 |
| Castor Oil, Hydrogenated (Elementris Specialties) | Emulsifier | 1-7 |
| Mixed Tocopherols - Vitamin E (Covi-Ox T-70, BASF) | Antioxidant | 0.05-1 |
| Fragrance (Lemongrass *Verbena* Fragrance Oil: New Directions) | Fragrance | 0.05-1 |
| Essential Oils Complex - other essential oils - mixture of one or more of Argan, Sesame, Jojoba, Grapeseed, Sweet Almond, Tea Tree Oil (Charkit Chemical Corporation) | Moisturizer | 0-5 |
| Glycerin, USP | Humectant | 0.5-3 |
| Walnut Shell 60/200, Sterilized (Composition Materials Co., Inc.) | Abrasive | 0.5-3 |
| Walnut Shell 35/60, Sterilized (Composition Materials Co., Inc.) | Abrasive | 0.5-3 |
| Diatomaceous Earth Perma Guard Fossil Shell Flour (Pure Diatomaceous Earth Prod) | Thickener | 0.5-3 |
| Fumed Silica Cab-O-Sil M5P, Pharma Grade (Cabot Corporation) | Thickener | 0.5-5 |
| Product Viscosity | | 4000-50,000 cps. |

The composition in Table 2B was prepared as follows. The coconut fractionated MTC and castor oil were added to a mixing vessel and mixed and heated. The mixture was mixed until the components appeared uniformly mixed. With agitation, the mixture was permitted to cool until the batch was below 35° C. The solvent and terpene were separately mixed until uniform and added to the mixture of coconut fractionated MTC and castor oil. Mixing was continued until the ingredients appeared homogenous. Stepwise addition of the other ingredients was performed with mixing to ensure uniform mixing.

TABLE 2B

Ingredients and concentration in an exemplary pediculicide.

| Chemical Component | Function | Concentration (wt. %) |
| --- | --- | --- |
| Fractionated Coconut Oil MTC-60/401 (New Directions Coconut Products) | Base Carrier | 70-90 |
| d-Limonene (Citrus-Solv ™ Prime, Florida Chemical) | Solvent | 3-7 |
| Castor Oil (Elementris Specialties) | Emulsifier | 1-5 |
| Mixed Tocopherols - Vitamin E (Covi-Ox T-70, BASF) | Antioxidant | 0.05-1 |
| Fragrance (Lemongrass *Verbena* Fragrance Oil: New Directions) | Fragrance | 0.05-1 |
| Essential Oils Complex - other essential oils - mixture of one or more of Argan, Sesame, Jojoba, Grapeseed, Sweet Almond, Tea Tree Oil | Moisturizer | 0-5 |
| Glycerin, USP | Humectant | 0.5-3 |
| Walnut Shell 60/200, Sterilized (Composition Materials Co., Inc.) | Abrasive | 0.5-3 |
| Walnut Shell 35/60, Sterilized (Composition Materials Co., Inc.) | Abrasive | 0.5-3 |
| Diatomaceous Earth Perma Guard Fossil Shell Flour (Pure Diatomaceous Earth Prod) | Thickener | 0.5-3 |
| Hydrogenated methyl abietate (Essential Ingredients) | Solubilizer | 1-5 |
| Product Viscosity | | 5000-65,000 cps. |

Example 2

Efficacy of Exemplary Composition and Methods of Use

Exemplary pediculicide compositions embodying a preferred embodiment of the invention were prepared and tested on human subjects with a lice infestation. The exemplary pediculicide composition was applied to the participants' hair and left in the hair undisturbed for 10 minutes. Then the hair was subjected to vigorous brushing with an applicator brush for five minutes. After brushing, the hair was left undisturbed again for 10 minutes. The hair was then rinsed, and the rinse water was collected. The rinse water was strained to collect lice from the rinse water. After the first rinse, the participants hair was combed with a fine-tooth lice comb and then washed with PRELL shampoo. The hair was brushed again and any additional lice were collected for examination.

All lice collected were examined to assess the condition of the lice. The lice collected included adult lice, nymphs (immature lice), and nits (lice eggs), which were primarily found crushed, shredded or otherwise deformed from the treatment. It is believed that the exemplary pediculicide composition was able to effectively shred or otherwise tear apart the lice during the treatment.

One-week after treatment the participants reported as to whether any additional lice were found, dead or alive. All participants reported finding additional dead lice after subsequent hair washing. One participant reported finding a single live adult louse. However, this was believed to be due to a reinfestation as no additional nymphs or nits were found, and which would have been present had the original infestation continued.

This demonstrated that the compositions and methods were effective at treating lice infestation and killing the lice, including, adults, nymphs, and nits. Further, it demonstrated that the compositions and methods were effective at removing the nits from the participants' hair follicles, which can be difficult to accomplish. None of the participants suffered from what believed to a continued infestation, indicating that the compositions were effective after only a single treatment.

While certain embodiments have been illustrated and described, it should be understood that changes and modifications can be made therein in accordance with ordinary skill in the art without departing from the technology in its broader aspects as defined in the following claims. The above specification provides a description of the manufacture and use of the disclosed compositions and methods. Since many embodiments can be made without departing from the spirit and scope of the invention, the invention resides in the claims.

What is claimed is:

1. A lice treating composition consisting essentially of: lice treating amounts of fractionated coconut oil, glycerin, diatomaceous earth, castor oil and an abrasive selected from the group consisting of stone, calcium carbonate, emery, impure corundum, diamond dust, pumice, sand, corundum, garnet, sandstone, powdered feldspar, staurolite, walnut shells, apricot pits, peach pits, nut shell, fruit pit polyethylene beads and mixtures thereof; and wherein the composition is in a form selected from the group consisting of a gel, cream and lotion.

2. The composition of claim 1, wherein the fractionated coconut oil is in an amount between about 60 wt. % and about 95 wt. % of the composition; wherein the abrasive is in an amount between about 0.5 wt. % and about 7 wt. % of the composition.

3. The composition of claim 2, wherein the diatomaceous earth is in an amount between about 0.5 wt. % and about 12 wt. % of the composition.

4. The composition of claim 1, wherein the composition has a viscosity between about 3500 cps and about 100,000 cps.

5. The composition of claim 3, wherein the composition further consists essentially of fused silica, a terpene, or a combination thereof.

6. The composition of claim 1, wherein the composition further consists essentially of a humectant 0.5 wt % to about 5 wt % selected from the group consisting of triethylene glycol, tripropylene glycol, propylene glycol, polypropylene glycol, glycerin, sorbitol, hexylene glycol, butylene glycol, collagen and mixtures thereof.

7. The composition of claim 1, wherein the composition further consists essentially of between about 1 wt. % and about 10 wt. % of a solvent; wherein the solvent selected from the group consisting of d-limonene, citrus oils, olive oil, and mixtures thereof.

8. The composition of claim 3, wherein the castor oil is in an amount between about 0.5 wt. % and about 10 wt. % of the composition.

9. The composition of claim 1, wherein the composition is free of a preservative.

10. A head lice treatment kit consisting essentially of:
(a) a pediculicide composition of lice treating amounts of fractionated coconut oil, glycerin, diatomaceous earth, castor oil and an abrasive selected from the group consisting of stone, calcium carbonate, emery, impure corundum, diamond dust, pumice, sand, corundum, garnet, sandstone, powdered feldspar, staurolite, walnut shells, apricot pits, peach pits, nut shell, fruit pit, polyethylene beads and mixtures thereof; and wherein the composition is in a form selected from the group consisting of a gel, cream and lotion; and wherein the pediculicide composition has a viscosity of between about 5000 cps and about 75,000 cps; and
(b) an applicator brush and/or lice comb.

11. The kit of claim 10, wherein the fractionated coconut oil is in an amount between about 60 wt. % and about 95 wt. % of the composition; wherein the abrasive is in an amount between about 0.5 wt. % and about 7 wt. % of the composition; wherein the diatomaceous earth is in an amount between about 0.5 wt. % and about 12 wt. % of the composition; and wherein the castor oil is in an amount between about 0.5 wt. % and about 10 wt. % of the composition.

12. The kit of claim 11, wherein the composition further consists essentially of between about 0.5 wt. % and about 5 wt. % of a humectant selected from the group consisting of triethylene glycol, tripropylene glycol, propylene glycol, polypropylene glycol, glycerin, sorbitol, hexylene glycol, butylene glycol, collagen, and mixtures thereof.

13. The kit of claim 12, wherein the composition further consists essentially of between about 1 wt. % and about 10 wt. % of a solvent; wherein the solvent is selected from the group consisting of d-limonene, citrus oils, olive oil, and mixtures thereof.

14. The kit of claim 10, wherein the composition is free of a preservative.

15. A method of preparing the lice treating composition of claim 4 consisting essentially of:
combining and mixing lice treating amounts of fractionated coconut oil, glycerin, diatomaceous earth, castor oil and an abrasive selected from the group consisting of stone, calcium carbonate, emery, impure corundum, diamond dust, pumice, sand, corundum, garnet, sandstone, powdered feldspar, staurolite, walnut shells, apricot pits, peach pits, nut shell, fruit pit, polyethylene beads and mixtures thereof; and
wherein the composition is in a form selected from the group consisting of a gel, cream and lotion.

16. The method of claim 15, wherein during the mixing the composition is heated.

* * * * *